United States Patent [19]
Finlan

[11] Patent Number: 4,886,360
[45] Date of Patent: Dec. 12, 1989

[54] METHOD AND APPARATUS FOR PARTICLE ANALYSIS

[75] Inventor: Martin F. Finlan, Aylesbury, England

[73] Assignee: Amersham International plc, Buckinghamshire, United Kingdom

[21] Appl. No.: 96,408

[22] Filed: Sep. 15, 1987

[30] Foreign Application Priority Data

Sep. 25, 1986 [GB] United Kingdom ............... 8623072

[51] Int. Cl.$^4$ .................. G01B 9/02; G01N 15/02
[52] U.S. Cl. .................................. 356/335; 356/345
[58] Field of Search ............................. 356/335, 345

[56] References Cited

U.S. PATENT DOCUMENTS 4,622,642 11/1986 Bajard et al. ................... 356/335 X

OTHER PUBLICATIONS

Witherow, "A high resolution holographic particle sizing system", *Optical Engineering*, vol. 18, No. 3, pp. 249-255, 6/79.

Primary Examiner—Davis L. Willis
Assistant Examiner—Matthew W. Koren
Attorney, Agent, or Firm—Wenderoth, Lind & Ponack

[57] ABSTRACT

The apparatus comprises a cell 2 containing the sample 1 under investigation. Electromagnetic waves P1,P2 are applied from opposite directions and interfere with one another in the region of the cell to form a standing wave pattern 6. Due to electrostriction effects the standing wave pattern causes particles within the sample to concentrate in certain areas in a pattern corresponding to that of the standing wave 6. This pattern of particle concentration forms a grating when seen by an input wave Pin of electromagnetic wave radiation and, provided conditions are correct, results in the generation of a phase conjugate wave Pout. Means (not shown) are provided for measuring the intensity of the phase conjugate wave Pout which gives a sensitive measure of the size of the particles suspended in the sample.

18 Claims, 1 Drawing Sheet

METHOD AND APPARATUS FOR PARTICLE ANALYSIS

This invention relates to a method and apparatus for particle analysis and is particularly concerned with analysis of the physical properties of particles suspended within a fluid medium.

As axample of such a substance is a chemical, biochemical or biological species suspended within a liquid for the purpose of assay. In order to perform an assay a material of a type capable of binding the species to be assayed is added. If binding occurs the sizes of the molecules of the binding pairs increases over their sizes prior to binding. If binding does not occur, no change in physical properties is observed. Thus analysis of the physical properties, in this case the size, of the molecules can determine whether or not the molecules have combined. The method and apparatus of the invention is able to carry out such analysis and, in a wider field, is able to analyse certain physical properties of any small particles suspended within a fluid medium.

According to the invention there is provided apparatus for particle analysis, said apparatus comprising a container made of electromagnetic radiation transparent material for containing a fluid sample to be analysed, means for setting up, within the sample, a stationary electromagnetic field comprising regions of high and low field intensity in a standing wave pattern in such a way as to establish within the sample a grating, means for applying to said grating an input wave of electromagnetic radiation in such a way as to cause said grating to generate a phase conjugate wave and means for measuring the intensity of said phase conjugate wave.

In the method of the invention two electromagnetic waves are caused to propagate towards one another in such a way as to interfere with one another in the region of the sample, thus creating a standing wave pattern of high and low field intensity. As a result of electrostrictive forces the particles within the fluid, having a different refractive index to that of the fluid, tend to concentrate in areas of higher or lower field intensity, leaving the remaining areas with a relatively weak concentration of particles or even no particles at all. The electrostrictive force is balanced by thermal diffusion (Brownian motion). Whether the particles concentrate in regions of high field intensity or in regions of low field intensity is dictated by the relative refractive index as between the particles and the fluid medium in which they are suspended. In the (probably more likely) event that the refractive index of the particles is greater than that of the fluid, then the particles will tend to concentrate in regions of high field intensity, leaving the regions of low intensity relatively denuded of particles. In the event that the refractive index of the particles is less than that of the fluid, the reverse situation occurs. It will be seen that, in either case, the concentration of spheres varies in the plane of the standing wave pattern in a pattern corresponding to that of the standing waves. This variation in concentration gives a corresponding variation in the effective dielectric constant of the sample and it is this that forms the grating used to generate the phase conjugate wave. The effectiveness of the grating in generating the phase conjugate wave is dependent upon the change in refractive index of the sample as between the areas of high and low field intensity; this in turn is dictated by the effectiveness with which the particles aggregate which is proportional to the product of the concentration of the particles and the sixth power of their radius. Although other physical characteristics of the particle can be detected, such as dielectric constant and refractive index, it will be seen from this that the size of the particles, as represented by their radius, strongly dictates the effectiveness of the grating, and hence the intensity of the phase conjugate wave generated thereby. Thus small changes in particle size can be monitored by observation of the phase conjugate wave, in particular its intensity. Furthermore it will be seen that absolute measurement of particle size can be made by empirical techniques.

A particular use of the invention is in the field of biological assays where the presence or absence of a particular species within a sample needs to be detected. This can be achieved by attempting to bind antigens within the sample, for example serum or saliva, with antibodies of a type capable of binding with the expected antigen. If binding occurs then the resultant molecule is increased in size over that which it would have if binding did not occur. A corresponding change also occurs in the dielectric constant and the refractive index of the particles. Thus the invention can be used to permit sensitive detection of changes in those physical properties of the particles as would come about if they were antibodies binding to antigens.

In certain circumstances, for example where the antibody molecules size is small, it may be desirable to "carry" the antibody on small, radiation-transplant, dielectric particles, for example spheres. In this case the sphere coated with antibody becomes the effective "particle" and will give a similar effect to that described above, but will be proportionately less sensitive since the effect is the result of the change in the size of the sphere plus antibody, rather than just the antibody itself.

A property which the sample needs to have in order to enable it to exhibit the phase conjugate phenomenon is that of non-linearity. By this is meant that the sample is inherently non-linear in its response to electromagnetic radiation; in particular in the variation of some inherent property of the sample—for example its refractive index—with the intensity of an applied radiation.

In an embodiment of the invention, an enhanced grating is formed by making the particles of a material which exhibits the optical Kerr effect. If this is done the particles, as well as aggregating due to electrostriction, as described above, will also, under the influence of the electric field portion of the electromagnetic standing wave, align themselves in such a way as to rotate the plane of polarisation of the aforesaid input wave of electromagnetic radiation. In this way the effectiveness of the grating in generating the phase conjugate wave can be enhanced.

In order that the invention may be better understood, an embodiment thereof will not be described by way of example only and with reference to the accompanying drawings in which.

Figure 1:
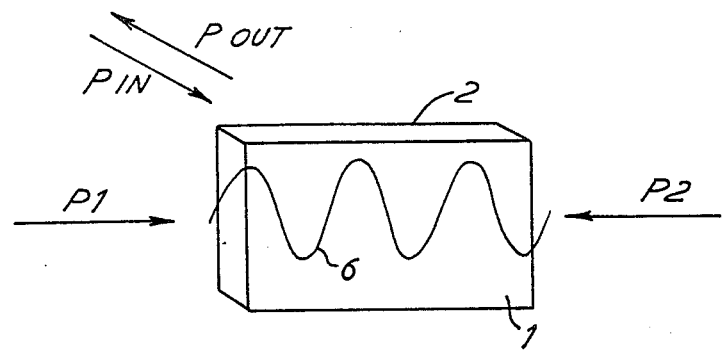
FIG. 1 is a drawing illustrating the basic principle of phase conjugation, as it applies to the present invention.
Figure 2:
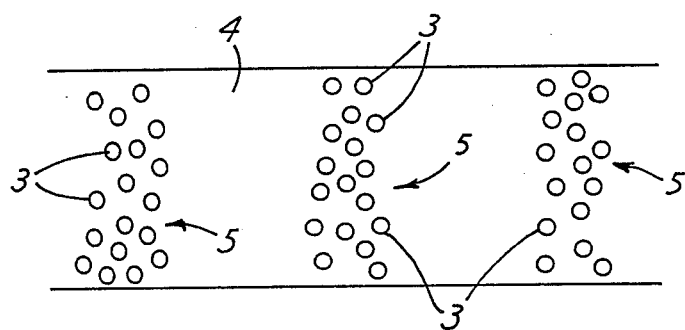
FIG. 2 is a diagram of the aggregation effect within the sample caused by electrostriction.

Referring to FIG. 1, the sample 1 to be analysed is contained within a cell represented diagrammatically under reference 2. In practice the cell could take the form of two plates of glass with a thin film of the sample, for example 100 microns thick, between. As shown in FIG. 2, the sample comprises a plurality of particles 3 suspended in a liquid, for example aqueous, medium 4. Both the liquid and the particles are transparent to the radiation to be applied—see below. For biochemical testing, examples of typical aqueous solutions are serum, urine or saliva; the particles may take the form of antibody molecules which are capable of binding suspected antigens in the liquid sample. The particles may alternately be dielectric, for example latex, bodies onto which antibody is coated. The bodies may be spherical in shape.

Prior to the application of radiation to the cell, the particles are uniformly distributed throughout the liquid. However, upon application of two pump waves P1, P2 of electromagnetic radiation (see FIG. 1), the particles aggregate into distinct groups 5 in the manner shown in FIG. 2. The pump waves are of identical frequency and are directed at one another in such a way as to cause a standing wave pattern of electric field, represented diagrammatically under reference 6, within the sample. In these circumstances, an electrorestrictive force is exerted on the particles 3, tending to cause them to move into regions of high electric field (where the refractive index of the particles is greater than that of the liquid) or into regions of low electric field (where the refractive index of the particles is less than that of the liquid). In either case, a distribution of the particles similar to that shown in FIG. 2 results, with the particles concentrated in certain areas with very few, if any, particles in the remaining areas. The electrorestrictive forces are in practice balanced by natural thermal diffusion. It follows from the above that, in order for the aggregation effect shown in FIG. 2 to take place, the refractive index of the particles 3 must be different to that of the liquid 4.

The effect of the particle aggregation is to increase the effective refractive index in the regions of high particle density and to reduce it in the regions of low particle density, thus creating a refractive index grating in the sample. An input wave $P_{in}$ of electromagnetic radiation may thus be applied to the grating at a suitable angle, typically in the region of 6 degrees, and will result in a zeroth-order phase conjugate wave $P_{out}$.

For particles whose radius r is much less than the wavelength λ of the incident radiation, the effectiveness of the grating in generating a phase conjugate wave is given by the Rayleigh scattering loss α o as follows:

$$\alpha_o = \frac{128 \pi^5 n_b^4}{3\lambda^4} \left( \frac{n^2 - 1}{n^2 + 2} \right)^2 r^6 N$$

where
$n = n_p/n_p$
$n_p$ = refractive index of particles
$n_b$ = refractive index of liquid
N = number of particles per unit volume of sample.

The above formula assumes that the particles are spherical and thus have a measurable radius; in practive non-spherical particles such as typical antibody molecules, will exhibit the same quantitative effect.

It will be noted that the effectiveness of the grating is proportional to the sixth power of the radius of the particles and detection of the intensity of the phase conjugate wave reflected from the grating can thus provide a very sensitive measure of the radius of the particles. The effectiveness is likewise proportional to the fourth power of the refractive index of the particles and this quantity can thus likewise be measured with great sensitivity. It is found that only a very small number of particles need to be present in each grating period to render the grating effective and the mechanism is thus effective even for very low particle concentrations.

It will be seen that the arrangement depicted diagrammatically in FIGS. 1 and 2 is capable of forming the basis of a very sensitive biochemical testing apparatus. By monitoring the intensity of the phase conjugate wave $P_{out}$, sensitive detection of such changes in physical properties of the particles as would come about if they were to be antibodies binding to antigens, or antibody coated bodies binding to antigens can be achieved. The effect will be seen in the liquid of the sample, directly with no pretreatment in vitro, and may be applicable non-invasively in vivo as, for example, via the ear lobe to the assessment of changes in circulating blood components.

Figure 3:
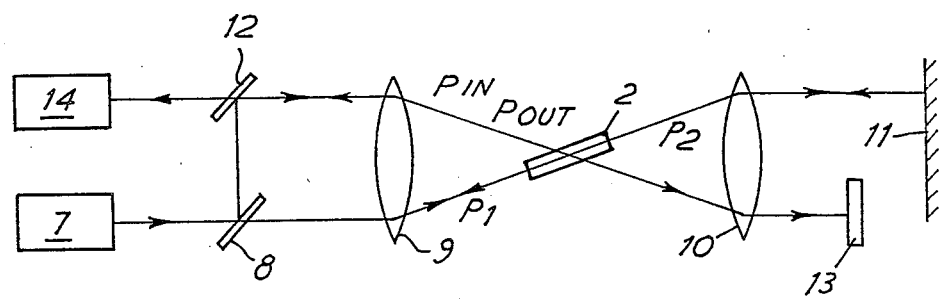
FIG. 3 is an illustrative block diagram of an embodiment of the apparatus of the invention.

In practice the two pump waves P1, P2, and the input wave $P_{in}$ are at the same frequency $\omega$. The resultant grating period corresponds to a standing wave of frequency $2\omega$. Typically the frequency used will be in the visible light range and by changing the frequency of the beams measurements can be made on particles of different dielectric constant. A particularly convenient apparatus for ensuring equality of frequency by utilising a single monochromatic source is illustrated diagrammatically in FIG. 3.

Radiation from a laser source 7 is directed through a first part-silvered mirror 8 thence refracted through a first lens 9 and second lens 10 to a mirror 11. The radiation is incident orthogonally on mirror 11 and thus reflects back upon itself, and retraces its path through lens 10, and lens 9 back to the mirror 8 where it is reflected to a second part-silvered mirror 12 back to the lens 9 and thence, crossing the original beam, through lens 10 to a radiation absorber 13.

Placed at the crossing point of the two beams is the cell 2 of FIG. 1. The forward and reflected rays entering the ends of the cell thus act as pump beams P1 and P2 and create a standing wave pattern of frequency $2\omega$ and a corresponding grating within the sample in the cell. The beam entering the cell after reflection from mirror 12 acts as the input beam $P_{in}$ and, if conditions are correct, will generate a phase conjugate wave back along the path of input wave $P_{in}$, through the lens 9 and mirror 12 to a radiation detector 14. Any radiation passing through the grating is absorbed by the radiation absorber 13, without being reflected.

The output of the radiation detector 14 is a measure of the intensity of the phase conjugate wave which in turn, as explained above, is a measure of the physical properties, in particular the radius or refractive index, of the particles within the sample in cell 2. In practice the change in the properties of the sample upon antibody/antigen binding will be compared with a standard in order to eliminate extraneous effects.

The mirror 11 may be replaced by a reflective surface attached to or forming part of a piezoelectric crystal. If the crystal is energised at a suitable frequency—say in the ultrasonic region, about 25 kHz the surface of the crystal will vibrate at this frequency and, if the radiation from the second lens 10 is reflected from this surface, the reflected radiation representing pump wave P2—will become phase modulated at the vibration frequency. This will cause the standing wave pattern set up within the cell 2 to oscillate backwards and forwards which will in turn cause the aggregated groups 5 particles 3 to likewise oscillate backwards and forwards. Thus the particles 3 are caused to move through the liquid medium 4 thus ensuring intimate mixing and speeding up the response of the apparatus.

I claim:

1. Apparatus for particle analysis, said apparatus comprising a container made of electromagnetic radiation transparent material for containing a fluid sample to be analysed, means for setting up, within the sample, a stationary electromagnetic field comprising regions of high and low field intensity in a standing wave pattern in such a way as to establish within the sample a grating, means for applying to said grating an input wave of electromagnetic radiation in such a way as to cause said grating to generate a phase conjugate wave and means for measuring the intensity of said phase conjugate wave.

2. Apparatus as claimed in claim 1 wherein said means for setting up a stationary electromagnetic field comprises first and second generators of electromagnetic waves, and means for directing the respective electromagnetic waves towards one another in such a way as to create a standing wave pattern in their region of interference within the sample.

3. Apparatus as claimed in claim 1 wherein said means for setting up a stationary electromagnetic field comprises an electromagnetic wave generator, means for splitting the output from said generator into two electromagnetic waves, and means for directing the two electromagnetic waves so formed towards one another in such a way as to create a standing wave pattern in their region of interference within the sample.

4. Apparatus as claimed in either one of claim 2 or 3 further comprising means for modulating at least one of said electromagnetic waves at a relatively low frequency so as to cause oscillation of the standing wave pattern and improve mixing of the particles within the sample.

5. Apparatus as claimed in claim 4 wherein the frequency of modulation is in the ultrasonic region.

6. A method for the analysis of particles suspended within a fluid medium, said method comprising setting up, within a sample, a stationary electromagnetic field comprising regions of high and low field intensity in a standing wave pattern in such a way as to establish within the sample a grating, applying to said grating an input wave of electromagnetic radiation in such a way as to cause said grating to generate a phase conjugate wave, and measuring the intensity of said phase conjugate wave.

7. A method as claimed in claim 6 wherein said stationary electromagnetic field is set up by causing two electromagnetic waves to propagate towards one another in such a way as to interfere with one another in the region of the sample.

8. A method as claimed in claim 7 wherein at least one of said electromagnetic waves is modulated at a lower frequency so as to cause the resultant standing wave pattern to oscillate.

9. A method as claimed in any one of claims 6, 7 or 8 wherein the particles to be detected are themselves carried by larger particles.

10. A method as claimed in claim 6 wherein the particles are made of a material which exhibits the optical Kerr effect.

11. A method as claimed in claim 6 wherein the sample comprises a chemical, biochemical or biological species suspended within a liquid and wherein, to perform an analysis, a material of a type capable of binding the species to be assayed is added.

12. A method as claimed in claim 7 wherein the particles are made of a material which exhibits the optical Kerr effect.

13. A method as claimed in claim 8 wherein the particles are made of a material which exhibits the optical Kerr effect.

14. A method as claimed in claim 9 wherein the particles are made of a material which exhibits the optical kerr effect.

15. A method as claimed in claim 7, wherein the sample comprises a chemical, biochemical or biological species suspended within a liquid and wherein, to perform an analysis, a material of a type capable of binding the species to be assayed is added.

16. A method as claimed in claim 8, wherein the sample comprises a chemical, biochemical or biological species suspended within a liquid and wherein, to perform an analysis, a material of a type capable of binding the species to be assayed is added.

17. A method as claimed in claim 9, wherein the sample comprises a chemical, biochemical or biological species suspended within a liquid and wherein, to perform an analysis, a material of a type capable of binding the species to be assayed is added.

18. A method as claimed in claim 10, wherein the sample comprises a chemical, biochemical or biological species suspended within a liquid and wherein, to perform an analysis, a material of a type capable of binding the species to be assayed is added.

* * * * *